United States Patent [19]

Austin et al.

[11] 4,314,088

[45] Feb. 2, 1982

[54] HYDROXYLATION OF OLEFINS

[75] Inventors: Richard G. Austin, Ridgewood; Robert C. Michaelson, Waldwick, both of N.J.

[73] Assignee: Exxon Research & Engineering Co., Florham Park, N.J.

[21] Appl. No.: 209,789

[22] Filed: Nov. 24, 1980

[51] Int. Cl.$^3$ .............................................. C07C 29/03
[52] U.S. Cl. .................................. 568/860; 260/346.3; 260/398; 568/811; 568/832; 568/833
[58] Field of Search ............... 568/860, 811, 832, 833; 260/398, 346.3

[56] References Cited

U.S. PATENT DOCUMENTS

| | | | |
|---|---|---|---|
| 2,414,385 | 1/1947 | Milas | 260/600 |
| 2,773,101 | 12/1956 | Smith et al. | 260/635 |
| 4,049,724 | 9/1977 | Sheng et al. | 260/635 H |
| 4,203,926 | 5/1980 | Wu et al. | 568/319 |

FOREIGN PATENT DOCUMENTS 54-145604 11/1979 Japan .

OTHER PUBLICATIONS

K. B. Sharpless in JACS, Mar. 31, 1976, pp. 1986–1987.
Akashi et al., "A Major Improvement in the Osmium Catalyzed Vicinal Hydroxylation of Olefins by t-Butyl Hydroperoxide", vol. 43, No. 10, pp. 2063–2066, (1978).

*Primary Examiner*—Joseph E. Evans
*Attorney, Agent, or Firm*—Roland A. Dexter; Robert A. Maggio

[57] ABSTRACT

Method for preparing polyols such as diols and triols by the homogeneous catalytic hydroxylation of an olefinic compound by contacting the olefinic compound with an organic hydroperoxide in an inert polar solvent containing catalytic amounts of an osmium compound and a halide and at least a stoichiometric amount of water based on the amount of said olefinic compound.

11 Claims, No Drawings

HYDROXYLATION OF OLEFINS

This invention relates to the Hydroxylation of Olefins with Organic Hydroperoxide Oxidant, Osmium Containing Catalyst and Halogen Containing Co-Catalyst. In particular, it relates to a procedure for reacting an olefin having 2 to 20 carbons, e.g. ethylene and propylene, with an organic hydroperoxide in the presence of an oxidation catalyst to produce the corresponding glycol.

BACKGROUND OF THE INVENTION

It is well known from the technical literature, including patents, that olefins can be effectively oxidized with osmium compounds, particularly osmium tetroxide, to their corresponding diols when the reaction is carried out with catalytic amounts of osmium tetroxide and a stoichiometric amount of a strong co-oxidizing agent. The oxidizing agents which have been proposed and used include the alkali metal chlorates and hypochlorites, potassium ferrocyanide and hydrogen peroxide (see U.S. Pat. Nos. 2,414,385 and 2,773,101, which use hydrogen peroxide with the latter teaching that inorganic peroxides, such as sodium and barium peroxides, or organic peroxides, such as tertiary butyl peroxide, tertiary butyl hydroperoxide, or benzoyl peroxide, can be used instead of the hydrogen peroxide).

Oxidation of $Os^{+6}$ to $Os^{+8}$ with molecular oxygen in aqueous alkaline solutions has also been reported, thus under these conditions olefins are oxidized to their corresponding diols at a pH in the range of 8.5–10.5 and to oxalic acid at a pH of 12.5. The reaction rate is slow, however, and the reaction ceases when the molar ratio of diol to osmium tetroxide exceeds 2. (See U.S. Pat. No. 4,049,724).

U.S. Pat. No. 4,049,724 improves the hydroxylation of olefins by homogeneous catalyzation relying on an aqueous solution of an organic hydroperoxide, e.g. t-butyl hydroperoxide, maintained at a pH of 8 to 12 by the presence of an appropriate amount of base, e.g., sodium carbonate. Low yields were reported and control of pH is necessary. This confirms the teaching of K. B. Sharpless in JACS, Mar. 31, 1976, pp. 1986–7 that whereas alkaline solutions of hydrogen peroxide decomposed violently in presence of $OsO_4$, solutions of t-butyl hydroperoxide in the presence of base (tetraethylammonium hydroxide gave yields superior to that obtained with sodium or potassium hydroxide) and $OsO_4$ were stable and provided good yields of vicinal diols from a variety of olefins.

Recently, U.S. Pat. No. 4,203,926 has taught the heterogeneous catalysis of ethylene and propylene to the corresponding glycol in a process in which ethylbenzene hydroperoxide is reacted with the olefin in a two-phase liquid (organic-aqueous) reaction system in the presence of osmium tetroxide and cesium, rubidium or potassium hydroxide. This two-phase system requires organic soluble hydroperoxides and appears specific for ethylbenzene hydroperoxide.

It is therefore an object of this invention to provide a new homogeneous catalysis method for the hydroxylation of olefins to generate valuable glycols.

SUMMARY OF THE INVENTION

It has been discovered that a polyol can be prepared by the hydroxylation of an olefin, such as ethylene or propylene, by contacting said olefin with t-butyl hydroperoxide in the presence of $OsO_4$, sodium bromide and tertbutyl alcohol containing at least a stoichiometric amount of water based on the amount of olefin.

Thus, in accordance with the object of this invention there has been provided a method for preparing polyols by the homogeneous catalytic hydroxylation of an olefinic compound having 2 to 20 carbons by contacting said olefinic compound with a catalytic amount of an osmium compound and a catalytic amount of a halide of the class consisting of an alkali metal or alkaline earth halide or a halogen in an inert polar solvent, an organic hydroperoxide and at least a stoichiometric amount of water based on said amount of said olefin.

DETAILED DESCRIPTION OF THE INVENTION

1. Olefinic Compound

The olefinic compounds which can be hydroxylated in accordance with this invention are those preferably having from 2 to 20 carbon atoms, including mono-olefinic compounds, diolefinic or polyolefinic compounds, both conjugated and non-conjugated, substituted and unsubstituted aliphatic and alicyclic olefins, hydroxy-substituted olefinic compounds, olefinically unsaturated aliphatic carboxylic acids and anhydrides, such as oleic acid, 1, 2, 3, 6-tetrahydrophthalic anhydride and the like. Illustrative olefins are butylene, pentenes, normal hexenes, the octenes, cyclohexene, butadiene, styrene, vinyl cyclohexene, and the like. The preferred olefinic compounds for this process are the $C_2$ to $C_4$ lower olefins, i.e. ethylene, propylene and butylene or allyl alcohol.

2. Catalysts (a) Osmium Tetroxide

The catalyst, osmium tetroxide, is used in catalytic quantities. It has been found that from 0.01 to ten millimols (mmols) the catalyst per 100 ml of the total reaction mixture is suitable; however, it is preferred to carry out the reaction from about 0.03 to about 0.1 mmol of catalyst per 100 ml of the reaction mixture. The amount of catalyst can also be related to the amount of osmium metal that is used. Thus, about 5 to about 1,000 ppm, preferably about 25 to about 800 ppm osmium can be used, based on the total liquid contents of the reaction vessel. The order of addition of catalyst is not critical to obtain high selectivities to glycols, since osmium does not catalyze the decomposition of the hydroperoxide in the olefin's absence.

Osmium tetroxide is readily soluble in organic polar solvent and can be dissolved in a said solvent for addition to the reactor.

(b) Halogen Compounds

The co-catalyst with the $OsO_4$ contains halogen and is a compound preferably of the class of alkali metal halides, alkaline earth halides, tetra alkyl or aryl phosphonium halide salts, or halogens; optimally, $I_2$, $NaI$, $KI$ and $HI$ or $Br_2$, $NaBr$, $KBr$ or $HBr$. The concentration of the co-catalyst halogen compound ranges from 5 to 100,000 ppm, preparably 10 to 100 ppm, based on the total liquid contents of the reaction vessel. The concentration of the co-catalyst halogen compound ranges from 1 to 1,000 times the amount of osmium.

3. Inert Polar Solvents

The inert polar solvents such as tertiary butyl alcohol, acetone, ethylene glycol, acetonitrile, diethylene glycol and dimethyl ether include organic polar solvents which can be an aliphatic or aromatic alcohol having from one to about ten carbon atoms, an aliphatic or aromatic ketone having from three to about ten carbon atoms, an aliphatic or alicyclic ether having from two to about ten carbon atoms, a glycol having from two to about ten carbon atoms, a N,N-dialkyl amide having from three to about ten carbon atoms, an aliphatic or aromatic sulfoxide having from two to about fourteen carbon atoms and an aliphatic or aromatic sulfone having from two to about fourteen carbon atoms. Examples of suitable polar solvents include methanol, ethanol, propanol, butanol, hexanol, decanol, benzyl alcohol, acetone, methylethyl ketone, methylbutyl ketone, acetophenone, ethylene glycol, propylene glycol, diethylene glycol, tetraethylene glycol, dimethyl formamide, diethyl formamide, dimethyl acetamide dimethyl sulfoxide, diethyl sulfoxide, di-n butyl sulfoxide, diphenyl sulfoxide, dibenzyl sulfoxide, dimethyl sulfone, diethyl sulfoxide, dibenzyl sulfoxide, diphenyl sulfone, acetonitrile, pyridine, dioxane, tetrahydrofuran, tetrahydropyran dioxolane, and the like. Preferred is acetonitrile, dioxane, acetone, carbon tetrachloride, dimethyl formamide, tetrahydrofuran, diethyl ether, primary alcohols such as methanol, ethanol, and isobutanol and tertiary alcohols such as tertiary butanol. Most preferred is a polar organic solvent with same carbon containing moiety as the hydroperoxide used, so as to minimize or avoid separation problems.

The amount of polar solvent can be between about 30 and 98 weight percent of the reaction mixture, but will preferably comprise between about 50 and 80 weight percent of the reaction mixture. The preferred organic polar solvents are those which resist oxidation in the reaction system and are miscible with water.

4. Organic Hydroperoxide

Although any organic hydroperoxide of the formula ROOH where R is a substituted or unsubstituted alkyl, cycloalkyl, aralkyl, azacyclic, or oxacyclic or 3 to 20 carbons would be operable, the preferred organic hydroperoxides are stable, most preferred are ethyl benzene hydroperoxide, tertiary butyl hydroperoxide and cumene hydroperoxide. Since frequently these hydroperoxides are made by the molecular oxygen oxidation of the corresponding hydrocarbons, there is also produced the corresponding alcohol. For example, when isobutane is oxidized with molecular oxygen there is produced tertiary butyl hydroperoxide and tertiary butyl alcohol. It is not necessary to separate the alcohol from the hydroperoxide since the alcohol can function merely as a diluent. The molar ratio of the hydroperoxide to olefinic compound can vary over a large range. Generally, molar ratios of olefin compounds in the substrates to hydroperoxide broadly in the range of 0.5:1 to 100:1, desirably 1:1 to 20:1 and preferably 2:1 to 10:1, are employed.

5. Water

It is believed that the hydroxylation of the olefin occurs according to the following reaction (using ethylene and t-butyl hydroperoxide as illustrative reactants):

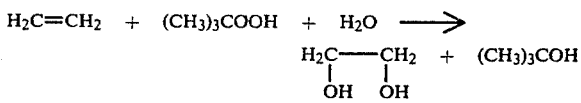

From this it is seen that the water is to be present in at least a stoichiometric amount based on the amount of olefin hydroxylated. Preferably, the amount of water ranges from 1.0 to 1.5 moles per molar quantity of olefin hydroxylated, although it can range from 1.0 to 10 moles per mole of said olefin.

Further, the hydroxylation reaction of the invention provides for the regeneration of the catalytic state of the osmium as a consequence of the halogen influence.

6. Reaction Conditions

Since the olefins to be hydroxylated, preferably ethylene and propylene, are gases, the olefin is incorporated into the reaction system by pressuring the reactor with the olefin. Although the magnitude of the pressure is not critical, it determines the amount of the olefin that is present in the reaction liquid and therefore affects the rate of reaction. It is believed that a pressure between about 5 and about 1,000 psig is useful for ethylene, and a pressure of between about 5 and about 150 psig is useful for propylene. However, it is preferred to operate within a pressure range of between about 50 and about 150 psig for ethylene and a pressure between about 10 and about 500 psig for propylene as providing a suitable reaction rate without requiring high pressure equipment. The reaction is preferably carried out with a stoichiometric excess of the olefin to substantially completely react all of the hydroperoxide in the reaction mixture, and more preferably, at least about a 25 percent stoichiometric excess of the olefin. It is advantageous to carry out reactions in the liquid phase; therefore, sufficient pressure is employed to maintain the reactants in the liquid phase, at least to the extent that some olefin is in the liquid phase. For liquid reactants, atmospheric pressure is suitable.

In practice, the osmium tetroxide is readily charged into the reaction vessel as a solution in the polar solvent, e.g., t-butanol, along with the halogen compound, inert polar solvent, hydroperoxide and water prior to pressuring the vessel with olefin. It is useful also to heat up the contents of the vessel prior to introduction of the olefin.

The hydroxylation reaction is carried out at a moderate temperature. At higher temperatures the reaction rate increases substantially but this occurs at a significant reduction in selectivity to the glycol. At very low temperatures, the selectivity to glycol is excellent but the reaction rate is slow. Within those constraints, it has been found that a moderate reaction temperature range of about −20° C. to about 200° C. is desirable and preferably ranges from 0° C. to 100° C. and optimally ranges from 25° C. to 50° C.

This hydroxylation reaction can be carried out as a batch reaction, or as a continuous reaction. In the batch reaction, all the necessary components are placed in a reaction vessel and the reaction is allowed to proceed for about ½ to about 2 hours for substantially complete reaction of the hydroperoxide. The reaction can be carried out in a continuous manner by metering the reaction components into an agitated tank reactor, or a series of tank reactors, pressured with the olefin and removing the reaction product mixture at an appropriate rate to maintain the reactor liquid level.

The reaction product mixture including inerts and by-products (after the removal of unreacted gaseous olefin) includes the diols, e.g. ethylene or propylene glycol, the polar solvent, the alcohol decomposition residue of the hydroperoxide, an osmium compound, the halogen compound and water but most important is a single phase mixture. Recovery of the product, e.g., ethylene glycol, is easily accomplished by fractional distillation.

This invention will be further understood by reference to the following examples which include the preferred embodiments and best mode of the invention.

EXAMPLE I

Into a 300 ml titanium autoclave is charged 0.023 g of osmium tetraoxide as a 0.5 weight percent t-butanol solution), 0.500 g sodium bromide, 54.9 g methanol and 11.1 g of tertiary butyl hydroperoxide (70%/$H_2O$). The solution is warmed to 40° C. and then ethylene (200 psig) is added. After stirring for 20 minutes, the product solution is analyzed by gas chromatography and indicates the production of 2.72 g of ethylene glycol which is a 54.9% yield based on the tertiary butyl hydroperoxide charged.

EXAMPLE II

Into a 300 ml titanium autoclave is charged 0.050 g of osmium tetraoxide (0.5%/t-butanol solution), 1.09 g sodium bromide, 46.0 g water, and 15.1 g of tertiary butyl hydroperoxide (70%/$H_2O$). To this solution is added 31.0 g of propylene and the reaction mixture is stirred at 25° C. for two hours. Propylene glycol (4.0 g) is produced in an amount which corresponds to a 48.0% yield based on the tertiary butyl hydroperoxide charged.

EXAMPLE III

Into a 300 ml titanium autoclave is charged 0.026 g of osmium tetraoxide (0.5%/t-butanol solution), 0.25 g sodium iodide, 66.6 g of methanol and 15.6 g of tertiary butyl hydroperoxide (70%/$H_2O$). The solution is warmed to 40° C. with stirring and ethylene (400 psig) is added. After stirring for thirty minutes, the reaction is cooled. Ethylene glycol (3.92 g) is produced in an amount indicating a yield of 54.5% based on the hydroperoxide charged.

EXAMPLE IV

Into a 300 ml titanium autoclave is charged 0.04 g $OsO_4$, 7.2 g t-butyl hydroperoxide (70%/$H_2O$), 0.50 g sodium bromide, 42.6 g t-butanol, and 3.0 g water. The contents are warmed to 40° C. and propylene (32.0 g) is added. The reaction is stirred at this temperature for thirty minutes. Propylene glycol (2.80 g) is produced in an amount corresponding to a yield of 65.7% based on tertiary hydroperoxide charged.

EXAMPLE V

A similar run to Example IV using sodium iodide in place of sodium bromide gave comparable yield of propylene glycol.

The invention in its broader aspect is not limited to the specific details shown and described and departures may be made from such details without departing from the principles of the invention and without sacrificing its chief advantages.

What is claimed is:

1. A method for preparing polyols by the homogeneous catalytic hydroxylation of an olefinic compound having 2 to 20 carbons by contacting said olefinic compound with a catalytic amount of an osmium compound and a "co-catalyst selected from the group consisting of an alkali metal halide, an alkaline earth metal halide, a halogen, a hydrogen halide, and a tetraalkyl or aryl phosphonium halide" in an inert polar solvent and an organic hydroperoxide and at least a stoichiometric amount of water based on said amount of said olefin.

2. A method according to claim 1 wherein said osmium compound is osmium tetroxide, the concentration of osmium is in the range of from 5 ppm to 1,000 ppm by weight, the concentration of said co-catalyst ranges from 1 to 1,000 times the amount of said osmium and the temperature ranges from 0° C. to 200° C.

3. The method according to claim 1 wherein said olefinic compound is ethylene.

4. The method according to claim 1 wherein said organic hydroperoxide is tertiary buty hydroperoxide.

5. The method according to claim 1 wherein said organic polar solvent is methanol.

6. The method according to claim 1 wherein said inert polar solvent is tertiary butyl alcohol.

7. The method according to claim 1 wherein said olefinic compound is propylene.

8. The method according to claim 1 wherein said olefinic compound is butylene.

9. The method according to claim 1 wherein said co-catalyst is iodine, sodium iodide, potassium iodide or hydrogen iodide.

10. The method according to claim 1 wherein said co-catalyst is bromine, sodium bromide, potassium bromide or hydrogen bromide.

11. The method according to claim 1 wherein said co-catalyst is tetraethylphosphonium bromide.

* * * * *